United States Patent [19]
Miguel

[11] Patent Number: 5,830,444
[45] Date of Patent: *Nov. 3, 1998

[54] ANHYDROUS SOLID DISPERSION CONTAINING ORGANOFLOURINATED HYDROCARBON COMPOUNDS AND ITS USE IN COSMETICS

[75] Inventor: Dolorés Miguel, Bourg-la-Reine, France

[73] Assignee: L'Oreal, Paris, France

[*] Notice: The term of this patent shall not extend beyond the expiration date of Pat. Nos. 5,702,689 and 5,705,165.

[21] Appl. No.: 584,702

[22] Filed: Jan. 11, 1996

Related U.S. Application Data

[63] Continuation of Ser. No. 188,424, Jan. 24, 1994, abandoned.

[30] Foreign Application Priority Data

Jan. 25, 1993 [FR] France .................................. 93 00911

[51] Int. Cl.⁶ .......................... A61K 7/027; A61K 7/035
[52] U.S. Cl. .............................. 424/64; 424/69; 424/401; 514/937
[58] Field of Search ................. 424/401, 64, 69; 514/937

[56] References Cited

U.S. PATENT DOCUMENTS 5,108,737  4/1992  Dunphy et al. ......................... 424/64

FOREIGN PATENT DOCUMENTS

| | | |
|---|---|---|
| 0 196 904 | 10/1986 | European Pat. Off. . |
| 0 390 206 | 10/1990 | European Pat. Off. . |
| 0 494 412 | 7/1992 | European Pat. Off. . |
| 0 524 892 | 1/1993 | European Pat. Off. . |
| 0 545 786 | 6/1993 | European Pat. Off. . |
| 62-223105 | 10/1987 | Japan . |
| WO93/11103 | 6/1993 | WIPO . |

OTHER PUBLICATIONS

Patent Abstracts of Japan, vol. 15, No. 068 (C–0807), 1991.

Patent Abstracts of Japan, vol. 016, No. 0409 C–0906, 1992.

Patent Abstracts of Japan, vol. 016, No. 315 (C–0961), 1992.

Patent Abstracts of Japan, vol. 012, No. 198 (C–502), 1988.

*Primary Examiner*—Jyothsna Venkat
*Attorney, Agent, or Firm*—Jacobson, Price, Holman & Stern, PLLC

[57] ABSTRACT

An anhydrous solid dispersion for use in cosmetics comprises, with respect to the total dispersion weight, 20 to 95%, preferably 40 to 85% by weight of a fatty substance constituted by 10 to 15% by weight of at least one wax having a melting point greater than 55° C., 0.5 to 50%, preferably 4 to 40% by weight of a dispersed polyhydric alcohol, and 0.1 to 50%, preferably 0.5 to 20% by weight of at least one organofluorinated hydrocarbon compound.

19 Claims, No Drawings

ANHYDROUS SOLID DISPERSION CONTAINING ORGANOFLOURINATED HYDROCARBON COMPOUNDS AND ITS USE IN COSMETICS

This is a continuation of application Ser. No. 08/188,424, filed Jan. 24, 1994, now abandoned.

BACKGROUND OF THE INVENTION

1. Field of the Invention

The present invention concerns anhydrous solid dispersions of polyols in an anhydrous medium containing organofluorinated hydrocarbon compounds and their use in cosmetics.

2. Description of the Prior Art

Solid fat cosmetic products are generally used in the cosmetics industry to produce lipsticks, in which case they are obtained by hardening fatty substances, and products such as foundations which are applied with a sponge and are obtained by mixing and compacting powders and fats.

Japanese patent application (publication number) JP-A-1 143 812 describes the incorporation of a substantial amount of polyvalent alcohols into a solid emulsion for cosmetic use using a silicone oil and a modified polyoxyalkylene organopolysiloxane as emulsifying agent. With this system, however, obtaining good homogeneity of the formula is difficult.

These products have the disadvantages of not being moisturisers.

It has previously been essential to disperse polyhydric alcohols in an anhydrous medium in order to prepare moisturising compositions, but these products have a tendency to become covered with droplets of fats, particularly in a damp atmosphere. The phenomenon of exudation is a disadvantage in that users find it highly repugnant.

The present invention overcomes the problem of exudation of solid dispersions of polyhydric alcohols in a fatty cosmetic medium. It has surprisingly been discovered that the introduction of fluorohydrocarbon type organofluorinated compounds can resolve the problem of exudation of solid dispersions containing polyhydric alcohols in a fatty phase.

SUMMARY OF THE INVENTION

The present invention concerns anhydrous solid dispersions containing from 20 to 95% of a substance constituted by 10 to 50% by weight of at least one wax having a melting point greater that 55° C., 0.5 to 50% by weight of a dispersed polyhydric alcohol and 0.1 to 50% by weight of organofluorinated hydrocarbon compounds.

Solid dispersion means a composition that is a solid between 0° and 50° C., the usual temperature range for storage and use of cosmetic products.

The organofluorinated compounds are fluorohydrocarbons which are non-volatile with a boiling point above 30° C.

Fluorohydrocarbon means compounds whose chemical structure comprises a carbon backbone where some hydrogen atoms have been substituted with fluorine atoms. The carbon backbone may comprise one or more heteroatoms and/or one or more functional organic groups.

The substitution ratio for replacement of hydrogen atoms with fluorine atoms is given as follows for fluorohydrocarbons: number of fluorine atoms/(number of fluorine atoms+ number of hydrogen atoms) where only those hydrogen atoms bonded to the carbon atoms of the backbone are taken into account. The fluorohydrocarbons or fluorohydrocarbonated oils of the invention comprise at least one hydrocarbon group in the molecule.

Fluorohydrocarbons in accordance with the invention have the following formula (I):

wherein:
- x is 1, 2 or 3,
- y is 0 or 1,
- z is 0, 1, 2 or 3, provided that y and z are not simultaneously 0 and that when z is 0 x is 2 or 3, $R_F$ is a fluorinated saturated or unsaturated aliphatic or aromatic radical with a linear, branched or cyclic chain which may be functionalized and/or interrupted by divalent atoms such as oxygen or sulfur or trivalent atoms such as nitrogen and/or substituted by hydrogen atoms or other halogen atoms provided that, for any two carbon atoms of the backbone, no more than one of these substituents other than fluorine is present, $R_H$ is a saturated or unsaturated aliphatic or aromatic hydrocarbon radical with a linear, branched or cyclic chain which may be functionalized and/or interrupted by one or more divalent atoms such as oxygen or sulfur or by one or more trivalent atoms such as nitrogen, A is a di-, tri- or quadrivalent radical such as

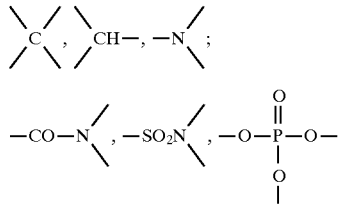

or a cyclic, aliphatic or aromatic group or an unsaturated ethylene group.

In the context of the invention functionalized means insertion or terminal or pendent substitution of the backbone by at least one organic functional group such as an alcohol, thiol, acid, carbonyl, sulfoxide, ester, amide, amine, phosphate, ethylene, acetylene, enamine or sulfonamide function.

Unsaturated ethylene structure means, for examples

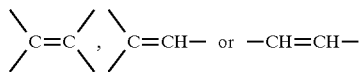

$R_H$ is preferably a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical.

$R_F$ is preferably a perfluoroalkyl radical having 4 to 22 carbon atoms.

In accordance with the invention, the fluorohydrocarbons used preferably have a substitution ratio of between 10 and 90%. This ratio is advantageously greater than 20% and less than 80%.

By way of illustration, compounds having perfluorocarbon groups and hydrocarbon groups can be mentioned, the total number of carbon atoms being between 10 and 30, the number of carbon atoms in the hydrocarbon groups being equal to or greater than twice the number of carbon atoms in the perfluorocarbon groups, as described in Japanese patent document JP 63-002916.

Also by way of illustration, the following fluorohydrocarbons described in French patent application 91 15 019 can be cited, wherein the general structure is defined by formula (III):

$$R_1-(CH_2)_n-X-[C_3H_5(OH)]-(Y)_x-R_2 \quad (III)$$

wherein $C_3H_5(OH)$ is the structure:

$$-CH_2-\underset{\underset{OH}{|}}{CH}-CH_2- \quad (Ia)$$

or $$-\underset{\underset{CH_2OH}{|}}{CH}-CH_2- \quad (Ib)$$

$R_1$ is a $C_4$–$C_{20}$ perfluoroinated radical or a mixture of $C_4$–$C_{20}$ perfluorinated alkyl radicals;

$R_2$ is a linear or branched $C_1$–$C_{22}$ alkyl radical or a mixture of linear or branched $C_1$–$C_{22}$ alkyl radicals or an aryl or an aralkyl radical;

n is between 0 and 4;

X is O, S,

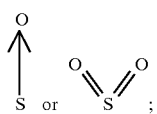

x is 0 or 1;

Y is O, S,

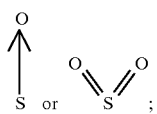

provided that when X is

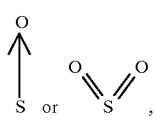

Y is not

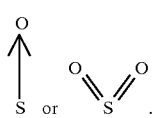

These compounds may be prepared either by reaction of a fluorinated compound with an acidic hydrogen atom of formula (II):

$$R_1-(CH_2)_n-X-H \quad (II)$$

with an epoxide having formula (II'):

$$R_2-(Y)_x-CH_2-\underset{O}{CH-CH_2} \quad (II')$$

or by reaction of a hydrocarbon compound with an acidic hydrogen atom of formula (IV):

$$R_2-(Y)_x-H \quad (IV)$$

with a fluorinated epoxide having formula (V):

$$R_1-(CH_2)_n-X-CH_2-\underset{O}{CH-CH_2} \quad (V)$$

wherein $R_1$, $R_2$, n and x have the meanings given above,

X is O or S, Y is O or S, in the presence of a basic or acidic compound acting as reactant or catalyst; oxidation if required of the mercaptan moiety to sulfoxide or sulfone with oxygenated water and recovery of the product obtained having formula (I). These compounds are described in WO 93/11103 and EP-A-0 166 696.

Examples of such compounds are as follows:
1-(2'-F-hexylethylthio)-3-(2"-ethylhexyloxy)-2-propanol,
1-(2'-F-octylethylthio)-3-(2"-ethylhexyloxy)-2-propanol,
1-(2'-F-octylethylthio)-3-butyloxy-2-propanol,
1-(2'-F-octylethylthio)-3-phenoxy-2-propanol,
1-(2'-F-hexylethylthio)-3-dodecyloxy-2-propanol,
1-(2'-F-hexylethylthio)-2-decanol,
1-(2'-F-hexylethylthio)-2-hexanol,
1-(2'-F-octylethylthio)-2-hexanol and
1-(2'-F-hexylethylthio)-3-(2"-ethylhexyloxy)-2-propanol.

Moreover, there may also be used according to the invention the compounds of formula (IV'):

$$R_F-(CH_2)_n-X-[C_3H_5(OH)]-Y-(CH_2)_m-R'_F \quad (IV')$$

in which $C_3H_5(OH)$ is the structure;

$$-CH_2-\underset{\underset{OH}{|}}{CH}-CH_2- \quad \text{or} \quad -\underset{\underset{CH_2OH}{|}}{CH}-CH_2-$$

or $$-CH_2-\underset{\underset{CH_2OH}{|}}{CH}-$$

$R_F$ and $R'_F$, which are identical or different, are a linear or branched perfluorinated $C_4$–$C_{20}$ alkyl radical or a mixture of linear or branched perfluorinated $C_4$–$C_{20}$ alkyl radicals;

m and n, which are identical or different, are 0, 1, 2, 3 or 4;

X and Y, which are identical, are —O— or —S—.

These compounds are described in DE-2 702 607, JP 89-193 236, JP 92-275 268 and U.S. Pat. No. 3,893,984.

There may also be used the compounds of formula:

$$R_F-(CH_2)_n-X-[C_3H_5(OH)]-Y-(CH_2)_m-R'_F \quad (I')$$

in which $C_3H_5(OH)$ is the structure:

$$-CH_2-\underset{\underset{OH}{|}}{CH}-CH_2- \quad (Ia)$$

or $$-CH-CH_2- \quad \text{(Ib)}$$
$$\quad | $$
$$\quad CH_2OH$$

or $$-CH_2-CH- \quad \text{(Ic)}$$
$$\quad\quad\quad | $$
$$\quad\quad\quad CH_2OH$$

$R_F$ and $R'_F$, which are identical or different, are a linear or branched perfluorinated $C_4-C_{20}$ alkyl radical or a mixture of linear or branched perfluorinated $C_4-C_{20}$ alkyl radicals;

m and n, which are identical or different, are 0, 1, 2, 3 or 4 and X is O and Y is S or X is S and Y is O.

The compounds of formula (I') can be prepared using the reaction of an acidic hydrogen-containing fluorinated compound of formula:

$$R_F-(CH_2)_n-X-H$$

with an epoxide of formula:

$$R'_F-(CH_2)_m-Y-CH_2-CH-CH_2$$
$$\quad\quad\quad\quad\quad\quad\quad\quad\quad \backslash\;/$$
$$\quad\quad\quad\quad\quad\quad\quad\quad\quad\;\; O$$

or the reaction of an acidic hydrogen-containing fluorinated compound of formula:

$$R_F-(CH_2)_m-Y-H$$

with a fluorinated epoxide of formula:

$$R_F-(CH_2)_n-X-CH_2-CH-CH_2$$
$$\quad\quad\quad\quad\quad\quad\quad\quad\quad \backslash\;/$$
$$\quad\quad\quad\quad\quad\quad\quad\quad\quad\;\; O$$

in the presence of a basic or acidic compound playing the part of reagent or catalyst. The compounds are described in FR 9 306 605.

There may also be used, according to the invention, the compounds described in the document DE 2 052 579, of formula:

$$R_F-CH_2-CH_2-X-CH_2-CH-Z \quad \text{(V')}$$
$$\quad\quad\quad\quad\quad\quad\quad\quad\quad\quad\quad\;\; |$$
$$\quad\quad\quad\quad\quad\quad\quad\quad\quad\quad\quad\;\; Y$$

where Y is OH, and

Z is

⟨phenyl⟩, $-CH_3$, $-CH_2OH$, $-CH_2OCOCH_3$ or alternatively Y is $-CH_2OH$ and Z is $-O-COCH_3$ X is $-O-$, $-S-$, $$\begin{array}{c} O \\ \uparrow \\ -S- \end{array} \quad \text{or} \quad \begin{array}{c} O\;\;\;O \\ \backslash\!\!/ \\ -S- \end{array},$$

and $R_F$ is a linear or branched perfluorinated $C_4-C_{20}$ alkyl radical or a mixture of linear or branched perfluorinated $C_4-C_{20}$ alkyl radicals;

or alternatively the compounds described in the document U.S. Pat. No. 3,952,066, of formula:

$$R_F-CH=CH-CH_2-O-CH_2-[C_2H_4-OW] \quad \text{(VI')}$$

where
$C_2H_4OW$ is:

$$-CH-CH_2W \quad \text{(a)}$$
$$\quad | $$
$$\quad OH$$

or $$-CH-CH_2OH \quad \text{(b)}$$
$$\quad | $$
$$\quad W$$

W is:

$-OR$, $-SR$, $-COOR$, $-O-$⟨phenyl⟩, $-O-$⟨phenyl-R'⟩

R is a linear or branched $C_1-C_{18}$ alkyl radical,

R' is $-CH_3$ or $-OH$, in the ortho or para position, and $R_F$ is a linear or branched perfluorinated $C_4-C_{20}$ alkyl radical or a mixture of linear or branched perfluorinated $C_4-C_{20}$ alkyl radicals.

In addition, products sold by NIPPON OIL & Co under the trade name NOFABLE FO having the following formula:

$$C_nF_{2n+1}-(CH_2)_p-O-\overset{O}{\overset{\|}{C}}-(CH_2)_7-CH=CH-(CH_2)_7-CH_3 \quad \text{(VI)}$$

wherein n is 6 or 8 and p is 1 or 2 can be cited by way of example. The compounds of formulae III and VI are preferred and particularly that of formula III where X is S, x is 1 and Y is O or X is S and x is O.

In accordance with a preferred embodiment of the invention, the solid dispersion of the invention may also contain up to 10% of an organic or mineral filler such as talc or starch, for example.

The dispersion of the invention may also contain up to about 30% (preferably 0.1 to 20%) of at least one pigment and from 0 to 20% (preferably 0.5 to 10%) of at least one surfactant.

The following surfactants generally used in lipsticks may be mentioned: anionic or non-ionic surfactants, with a HLB (Hydrophilic-Lipophilic Balance) of less than 10 (preferably less than 5) excluding siliconized surfactants. Among non-ionic surfactants, lecithins and succinylglycerides may be mentioned.

The following anionic surfactants may be mentioned: alkylphosphates, magnesium lanolate, zinc lanolate, copper lanolate, arginine lanolate and magnesium octadecanoate.

The surfactant produces a finer and more stable dispersion.

In accordance with a particularly preferred embodiment of the invention, a polymer is added to the dispersion of the invention in a quantity sufficient to further stabilize it against exudation in a damp atmosphere.

Such polymers are preferably liposoluble and have a low proportion of hydrophilic moieties.

The following polymers may be mentioned: polyalkylenes (in particular polyethylenes and polybutenes), polyacrylates and silicone polymers which are compatible with the fatty substances, such as polysteanylmethylsiloxane sold by GOLDSCHMIDT under the trade name ABIL WAX 9800.

The following polyalkylenes may be mentioned: polybutene, in particular that sold by AMOCO under the trade name INDOPOL.

In accordance with the invention, the polyhydric alcohol may be a compound having two to eight carbon atoms and two to six hydroxyl functions. Among these compounds, the following may be mentioned: ethylene glycol, glycerol, propane-1,2-diol, diglycerine, erythritol, arabitol, adonitol, sorbitol or dulcitol.

The polyhydric alcohol may also be a polyether alcohol having an average molecular weight of between 150 and 600. Among these, polyethylene glycol (300) and polyglycerines (500) may be mentioned.

In accordance with the invention, when the organofluorinated hydrocarbon compound is functionalized with OH, SH, NH or $NH_2$ groups, the polyol comprises at least three hydroxyl functions.

The polyhydric alcohol phase of the dispersion in accordance with the invention may be enriched with hydrosoluble ingredients such as amino acids (for example Arginine, Lysine, hydroxyproline, Proline and Serine), glycerine-soluble vitamins such as D, L-Panthenol and compatible solar filters. These may be present in amounts of 0.05 to 5%.

The fatty substance in accordance with the invention is constituted by 10 to 50% by weight of at least one wax having a melting point greater than 55° C., the remainder being a wax having a melting point less than 55° C. or an oil or a mixture of the two, the end melting point of the mixture being less than 110° C. This does not prevent some of the constituents of the mixture from having a higher melting point.

The following waxes having a melting point greater than 55° C. which may be employed in the present invention may be mentioned: animal, plant, mineral, synthetic waxes and numerous fractions of natural waxes, in general all waxes with a melting point between 55° and 110° C. and a needle penetration at 25° C. of between 3 and 40 as measured in accordance with US standard ASTM D5 or French standard NFT 004.

The technique of measuring needle penetration according to these two standards consists in measuring the depth in tenths of a millimeter to which a standardized needle (weight 2.5 g in a needle carrier weighing 47.5 g, i.e., total weight 50 g) will penetrate into the wax in five seconds.

Among animal waxes which may be used the following may be mentioned: beeswax, lanolin wax and lanoline derivatives. Among plant waxes the following may be mentioned: Carnauba wax, Candelilla wax, Ouricury wax, cork fibre wax, sugar cane wax and Japan wax. Among mineral waxes the following may be mentioned, in particular: paraffins, microcrystalline waxes, lignite waxes and ozokerites. Among synthetic waxes the following may be mentioned, in particular: polyethylene waxes, waxes obtained from Fischer-Tropsch synthesis and waxy polymers and their esters. These waxes are all well known to the person skilled in the art.

The following oils which may be used mixed with waxes may in particular be mentioned:

mineral oils such as paraffin oil, vaseline oil and mineral oils with a boiling point between 310° and 410° C.;

oils of animal origin such as perhydrosqualene;

plant oils such as sweet almond oil, calophyllum oil, palm oil, avocado oil, jojoba oil, olive oil, castor oil, cereal germ oils such as wheatgerm oil;

silicone oils such as dimethylpolysiloxane, synthetic esters such as Purcelin oil, butyl myristate, isopropyl myristate, cetyl myristate, isopropyl palminate, butyl stearate, hexadecyl stearate, isopropyl stearate, octyl stearate, isocetyl stearate, decyl oleate, hexyl laurate, propylene glycol dicaparylate, diisopropyl adipate;

organic alcohols compatible with the fatty substance such as oleic alcohol, linoleic alcohol, isostearyl alcohol, octyl dodecanol;

esters derived from lanolic acid such as isopropyl lanolate and isocetyl lanolate.

The following oils may also be mentioned: acetylglycerides, octanoates and decanoates of alcohols and polyalcohols such as those of glycol and glycerol, alcohol and polyalcohol ricinoleates such as those of cetyl alcohol.

Hydrogenated oils which are solids at 25° C. may be added as the fatty substance. Examples are hydrogenated castor oil, hydrogenated palm oil, hydrogenated tallow, hydrogenated coconut oil, fatty esters which are solids at 25° C. such as propylene glycol myristate and myristyl myristate, cetyl alcohol, mono-, di- or triglycerides and sucroglycerides.

In addition, this fatty phase may contain pigments. The following colored pigments may be mentioned: carbon black or black iron oxide, chromium oxides, yellow and red iron oxides, ultramarines (aluminosilicate polysulfides), manganese pyrophosphate, ferric blue, titanium dioxide and some powdered metals such as silver or aluminum. The pigments are most often used mixed with pearlising agents such as bismuth oxychloride, micatitanium, guanine crystals and some organic dyes such as cochineal carmine and organic lacquers.

These lacquers, which are routinely used to give the lips and skin a made up look are calcium, barium, aluminum or zirconium salts and acid dyes such as halogeno-acid, azo or anthraquinone dyes, for example.

The following lacquers may in particular be mentioned: those known under the denominations D and C Red 21, D and C Orange 5, D and C Red 27, D and C Orange 10, D and C Red 3, D and C Red 7, D and C Red 2, D and C Red 4, D and C Red 8, D and C Red 33, D and C Yellow 5, D and C Yellow 6, D and C Green 5, D and C Yellow 10, D and C Green 3, D and C Blue 1, D and C Blue 2, D and C Violet 1, for example.

Cosmetic makeup compositions in accordance with the invention may also contain antioxidizing agents in an amount of 0 to 3%, preferably 0.05 to 0.5%, such as propyl, octyl and dodecyl esters of gallic acid, butylhydroxytoluene and butylhydroxyanisole, as well as perfume and preservatives such as methyl or propyl parahydroxybenzoate. These additives may be in either the fatty phase or the polyhydric alcohol dispersed phase, depending on their solubility.

The lipophile phase may contain one or more liposoluble ingredients commonly used in cosmetic or pharmaceutical products, in amounts of 0.05 to 5%, preferably 0.5 to 3%.

Among these, the following may be mentioned: vitamin derivatives such as tocopherol acetate and the palmitate of vitamin A, essential fatty acids, sphingocerils, ceramides and soluble solar filters.

Compositions in accordance with the invention are generally prepared by a method comprising the following steps:

the fatty phase constituted by at least one oil and at least one wax, the organofluorinated hydrocarbon compound and if necessary a dispersion of pigments and/or fillers is heated to a temperature above the highest melting point of the waxes (end temperature), and the polyhydric alcohol containing soluble additives if required is if necessary heated separately to the same temperature and the two constituents are mixed.

The emulsion thus obtained is then cast into an appropriate mould.

The invention also concerns the use of dispersions in accordance with the invention in the cosmetic and dermatological fields.

DETAILED DESCRIPTION OF THE INVENTION

PREPARATION EXAMPLES

Example A
1-(2'-F-hexylethylthio)-3-(2"-ethylhexyloxy)-2-propanol 3.6 g of a methanolic solution of sodium methylate (about 30%—5.54 meq g$^{-1}$) was added over one minute to 152 g of 2-F-hexylethanethiol at a temperature of 25° C., with stirring and in a current of nitrogen.

The mixture was heated to 70° C. The methanol present in the mixture was vacuum evaporated.

2-ethylhexylglycidyl ether (74.4 g) was then added dropwise over one hour. The mixture temperature was maintained between 60° and 70° C. during addition of the epoxide.

The temperature was reduced to 25° C. following addition.

The mixture was neutralized using 20 ml of normal HCl.
1-(2'-F-hexylethylthio)-3-(2"-ethylhexyloxy)-2-propanol was separated by distillation:
BPt=141° C./66.5 Pa.

175 g (77%) of a colorless translucent oil was obtained.

| | Elementary analysis | | | |
|---|---|---|---|---|
| Calculated | 40.28 | 4.80 | 5.66 | 43.60 |
| Measured | 40.37 | 4.82 | 5.55 | 43.74 |

Example B
1-(2'-F-octylethylthio)-2-hexaol 30 g (0.3 mole) of 1,2-epoxyhexane was condensed with 144 g (0.3 mole) of 2-F-octylethanethiol in the presence of 2.7 g of a methanolic solution of sodium methylate (5.65 meq g$^{-1}$) over one hour using the method described in example A.

At the end of the reaction the mixture was neutralized with 15 ml of normal HCl.

Following distillation, (154° C./133 Pa) 115 g of an amorphous white solid was obtained. This was 1-(2'-F-octylethylthio)2-hexanol.

Yield=67%. Melting point=45° C.

| | %C | %H | %S | %F |
|---|---|---|---|---|
| Calculated | 33.11 | 2.95 | 5.53 | 55.65 |
| Measured | 33.26 | 2.93 | 5.30 | 55.60 |

FORMULATION EXAMPLES

Example 1—Lipstick

| | |
|---|---|
| Castor oil | 13.75 g |
| Sesame oil | 13.75 g |
| Acetylated lanoline | 30 g |
| Butylhydroxytoluene | 0.2 g |
| Beeswax | 8 g |
| Carnauba wax | 6 g |
| Trioleyl phosphate | 1 g |
| Glycerine | 16 g |
| Titanium oxide | 2 g |
| FD & C Yellow 6 Aluminum Lake | 3 g |
| D & C Red 7 Calcium Lake | 5.8 g |
| 1-(2'-F-hexylethylthio)-3-(2"-ethylhexyloxy)2-propanol (Example A) | 0.5 g |
| Perfume | qs |

Example 2—Lipstick

| | |
|---|---|
| Castor oil | 13 g |
| Sesame oil | 13 g |
| Acetylated lanoline | 30 g |
| Butylhydroxytoluene | 0.2 g |
| Beeswax | 8 g |
| Carnauba wax | 6 g |
| Trioleyl phosphate | 1 g |
| Glycerine | 16 g |
| Titanium oxide | 2 g |
| FD & C Yellow 6 Aluminum Lake | 3 g |
| D & C Red 7 Calcium Lake | 5.8 g |
| 1-(2'-F-hexylethylthio)-3-(2"1-ethylhexyloxy)2-propanol (Example A) | 2 g |
| Perfume | qs |

Example 3—Lipstick

| | |
|---|---|
| Castor oil | 6 g |
| Sesame oil | 6 g |
| Acetylated lanoline | 6 g |
| Butylhydroxytoluene | 0.2 g |
| Beeswax | 6 g |
| Carnauba wax | 6 g |
| Trioleyl phosphate | 1 g |
| Glycerine | 16 g |
| Titanium oxide | 2 g |
| FD & C Yellow 6 Aluminum Lake | 3 g |
| D & C Red 7 Calcium Lake | 5.8 g |
| 1-(2'-F-hexylethylthio)-3-(2"-ethylhexyloxy)2-propanol (Example A) | 40 g |
| Perfume | qs |

Example 4—Lipstick

| | |
|---|---|
| Triglycerides of capric/caprylic acids, sold by HULS under the trade name MIGLYOL 812 | 9 g |
| Sesame oil | 14 g |
| Isopropyl lanolate | 34 g |
| Butylhydroxytoluene | 0.2 g |
| Carnauba wax | 5 g |
| Polyethylene wax | 8 g |
| Glycerine | 16 g |
| Titanium oxide | 2 g |
| FD & C Yellow 6 Aluminum Lake | 3 g |
| D & C Red 7 Calcium Lake | 5.8 g |
| 1-(2'-F-hexylethylthio)-3- | 3 g |

-continued

| | |
|---|---|
| (2"-ethylhexyloxy)2-propanol (Example A) | 3 g |
| Perfume | qs |

Example 5—Lipstick

| | |
|---|---|
| Sesame oil | 15 g |
| Vaseline oil | 23 g |
| Lanoline | 20 g |
| Butylhydroxytoluene | 0.2 g |
| Microcrystalline wax | 10 g |
| Carnauba wax | 3 g |
| Soya lecithin | 1 g |
| Glycerine | 12 g |
| D & C Red 27 | 5 g |
| Black iron oxide | 0.2 g |
| D & C Red 7 Calcium Lake | 5.6 g |
| 1,1,2,2-tetrahydroheptadecafluoro-1-decanol oleate (Nofable FO-9982 from Nippon Oil Fats) | 5 g |

Example 6—Lipstick

| | |
|---|---|
| Jojoba oil | 7 g |
| Sesame oil | 10 g |
| Isopropyl lanolate | 16 g |
| Butylhydroxytoluene | 0.2 g |
| Ozokerite | 8 g |
| Beeswax | 8 g |
| Polybutene (INDOPOL from AMOCO) | 10 g |
| Trioleyl phosphate | 2 g |
| Polyglycerine 500 | 16 g |
| FD & C Yellow 6 Aluminum Lake | 1 g |
| D & C Red 27 | 9 g |
| Titanium dioxide | 2.8 g |
| 1-(2'-F-hexyethylthio)-3-(2"-ethylhexyloxy)2-propanol (Example A) | 10 g 10 g |

Example 7—Lipstick

| | |
|---|---|
| Castor oil | 5 g |
| Vaseline oil | 20 g |
| Lanoline | 10 g |
| Isopropyl lanolate | 25 g |
| Magnesium lanolate | 4 g |
| Butylhydroxytoluene | 0.2 g |
| Carnauba wax | 2.8 g |
| Microcrystalline wax | 15 g |
| Glycerine | 3 g |
| 2-perfluorohexyl ethanol | 5 g |
| Pigments | 10 g |

Example 8—Lipstick

| | |
|---|---|
| Jojoba oil | 7 g |
| Sesame oil | 10 g |
| Isopropyl lanolate | 9 g |
| Butylhydroxytoluene | 0.2 g |
| Ozokerite | 8 g |
| Beeswax | 8 g |
| Polybutene | 10 g |
| Trioleyl phosphate | 2 g |
| Polyglycerine 500 | 25 g |
| FD & C Yellow 6 Aluminum Lake | 1 g |
| D & C Red 27 | 9 g |
| Titanium dioxide | 2.8 g |

-continued

| | |
|---|---|
| 1-(2'-F-hexylethylthio)-3-(2"-ethylhexyloxy)2-propanol (Example A) | 8 g |

Example 9—Foundation

| | |
|---|---|
| Microcrystalline wax | 8 g |
| Carnauba wax | 4 g |
| Octyl palmitate | 14.5 g |
| Isoparaffin | 23 g |
| Isopropyl lanolate | 4 g |
| Propyl parahydroxybenzoate | 0.2 g |
| Yellow iron oxide | 1 g |
| Brown iron oxide | 0.37 g |
| Black iron oxide | 0.15 g |
| Titanium oxide | 5.47 g |
| Zinc oxide | 3 g |
| Talc | 3 g |
| Powdered nylon | 3 g |
| Microspheres sold by KEMANORD PLAST AB under the trade name EXPANCEL DE | 1.2 g |
| Dimethicone | 0.3 g |
| Vinyl polylaurate | 12.5 g |
| Glycerine | 12 g |
| Magnesium lanolate | 1 g |
| 1-(2'F-octylethylthio)-2-hexanol (Example B) | 3 g |
| Perfume | 0.31 g |

COMPARATIVE EXAMPLES

Comparative Example 1

| | |
|---|---|
| Castor oil | 14 g |
| Sesame oil | 14 g |
| Acetylated lanoline | 30 g |
| Butylhydroxytoluene | 0.2 g |
| Beeswax | 8 g |
| Carnauba wax | 6 g |
| Trioleyl phosphate (for example Hosphat KO 300 from Hoechst) | 1 g |
| Glycerine | 16 g |
| Titanium oxide | 2 g |
| FD & C Yellow 6 Aluminum Lake | 3 g |
| D & C Red 7 Calcium Lake | 5.8 g |
| Perfume | qs |

Comparative Example 2

| | |
|---|---|
| Triglycerides of capric/caprylic acids, sold by HULS under the trade name MIGLYOL 812 | 10 g |
| Sesame oil | 15 g |
| Isopropyl lanolate | 35 g |
| Butylhydroxytoluene | 0.2 g |
| Carnauba wax | 5 g |
| Polyethylene wax | 8 g |
| Glycerine | 16 g |
| Titanium oxide | 2 g |
| FD & C Yellow 6 Aluminum Lake | 3 g |
| D & C Red 7 Calcium Lake | 5.8 g |
| Perfume | qs |

After one day sticks of the comparative examples exuded and were covered with droplets.

After one month sticks in accordance with the invention still had no droplets on them.

There is claimed:

1. Anhydrous solid dispersion comprising:

20 to 95% by weight with respect to the total dispersion weight of a fatty substance constituted by 10 to 50% by weight of at least one wax having a melting point greater than 55° C., 0.5 to 50% by weight with respect to the total dispersion weight of a dispersed polyhydric alcohol, and 0.1 to 50% by weight with respect to the total dispersion weight of at least one organofluorinated hydrocarbon compound, the organofluorinated hydrocarbon compound having a substitution ratio of between 10 and 90%, the polyhydric alcohol having at least three hydroxyl functional groups when the organofluorinated hydrocarbon compound is functionalized with OH, SH, NH or $NH_2$ groups, and the organofluorinated hydrocarbon compound having the following formula (I):

$$R_F-R_H \qquad (I)$$

wherein $R_F$ is a fluorinated saturated or unsaturated $C_4$–$C_{22}$ aliphatic radical with a linear or branched chain which may be functionalized by insertion, terminal or pendant substitution of the backbone by at least one organic functional group selected from the group consisting of an alcohol, thiol, acid, carbonyl, sulfoxide, ester, amide, amine, phosphate and sulfonamide, or interrupted by one or more oxygen or sulfur atoms, and $R_H$ is a saturated or unsaturated $C_1$–$C_{22}$ aliphatic hydrocarbon radical with a linear or branched chain which may be functionalized by insertion, terminal or pendant substitution of the backbone by at least one organic functional group selected from the group consisting of an alcohol, thiol, acid, carbonyl, sulfoxide, ester, amide, amine, phosphate and sulfonamide, or interrupted by one or more oxygen or sulfur atoms.

2. Dispersion according to claim 1 wherein the organofluorinated hydrocarbon compound has the following formula (III):

wherein $C_3H_5(OH)$ is the structure:

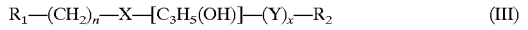

or

$R_1$ is a $C_4$–$C_{20}$ perfluorinated radical or a mixture of $C_4$–$C_{20}$ perfluorinated alkyl radicals;

$R_2$ is a linear or branched $C_1$–$C_{22}$ alkyl radical or a mixture of linear or branched $C_1$–$C_{22}$ alkyl radicals or an $C_6$–$C_{10}$ aryl or $C_7$–$C_{15}$ aralkyl radical;

n is between 0 and 4;

X is O, S,

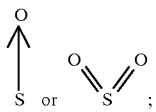

x is 0 or 1;

Y is O, S,

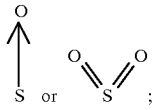

provided that when X is

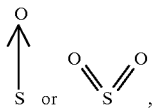

Y is not S

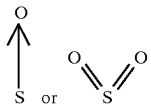

or formula (VI):

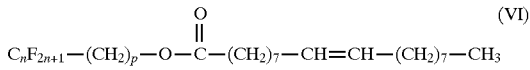

wherein n is 6 or 8 and p is 1 or 2.

3. Dispersion according to claim 1 wherein the polyhydric alcohol is a compound having two to eight carbon atoms and two to six hydroxyl functions or a polyether alcohol having an average molecular weight of between 150 and 600.

4. Dispersion according to claim 1 containing up to 20% by total weight with respect to the total dispersion weight of a surfactant.

5. Dispersion according to claim 1 wherein the polyhydric alcohol contains hydrosoluble ingredients in a concentration between 0.05 and 5% by weight with respect to the total dispersion weight.

6. Dispersion according to claim 1 further comprising at least one polymer for stabilizing the dispersion in a damp atmosphere.

7. Dispersion according to claim 1 containing up to 30% by weight with respect to the total dispersion weight of at least one pigment.

8. Dispersion according to claim 1 containing up to 10% by weight with respect to the total dispersion weight of at least one mineral filler.

9. A cosmetic composition containing an anhydrous solid dispersion according to claim 1.

10. Dispersion according to claim 1 wherein the fatty substance constituted by 10 to 50% by weight of at least one wax having a melting point greater than 55° C. comprises 40 to 85% by weight with respect to the total dispersion weight.

11. Dispersion according to claim 1 wherein the dispersed alcohol comprises 4 to 40% by weight with respect to the total dispersion weight.

12. Dispersion according to claim 1 wherein the at least one organofluorinated hydrocarbon compound comprises 0.5 to 20% by weight with respect to the total dispersion weight.

13. Dispersion according to claim 1 wherein $R_F$ is a fluorinated saturated aliphatic linear radical having 4 to 22 carbon atoms and $R_H$ is an unsaturated aliphatic linear $C_2$–$C_{22}$ hydrocarbon radical or a mixture of unsaturated aliphatic linear $C_2$–$C_{22}$ hydrocarbon radicals functionalized by terminal substitution of the backbone of an ester group.

14. Dispersion according to claim 1 which is a lipstick or a solid foundation.

15. Dispersion according to claim 1 which further contains a wax having a melting point less than 55° C. or an oil or a mixture of said wax and oil.

16. Dispersion according to claim 15 wherein the oil is a silicone oil.

17. Dispersion according to claim 16 wherein the silicone oil is a dimethylpolysiloxane.

18. Dispersion according to claim 1 which further contains 0.5 to 10% by weight of an anionic or non-ionic surfactant with a HLB of less than 10.

19. Method for avoiding exudation of a solid dispersion of a polyhydric alcohol in a fatty cosmetic medium comprising the step of introducing into said solid dispersion an effective amount of an organofluorinated hydrocarbon compound having the following formula:

$$R_F\text{—}R_H \qquad (I)$$

wherein $R_F$ is a fluorinated saturated or unsaturated $C_4$–$C_{22}$ aliphatic radical with a linear or branched chain which may be functionalized by insertion, terminal or pendant substitution of the backbone by at least one organic functional group selected from the group consisting of an alcohol, thiol, acid, carbonyl, sulfoxide, ester, amide, amine, phosphate and sulfonamide, or interrupted by one or more oxygen or sulfur atoms, and $R_H$ is a saturated or unsaturated $C_1$–$C_{22}$ aliphatic hydrocarbon radical with a linear or branched chain which may be functionalized by insertion, terminal or pendant substitution of the backbone by at least one organic functional group selected from the group consisting of an alcohol, thiol, acid, carbonyl, sulfoxide, ester, amide, amine, phosphate and sulfonamide, or interrupted by one or more oxygen or sulfur atoms.

* * * * *